(12) United States Patent
Dai et al.

(10) Patent No.: US 6,346,189 B1
(45) Date of Patent: *Feb. 12, 2002

(54) CARBON NANOTUBE STRUCTURES MADE USING CATALYST ISLANDS

(75) Inventors: Hongjie Dai, Sunnyvale; Calvin F. Quate, Stanford; Hyongsok Soh, Stanford; Jing Kong, Stanford, all of CA (US)

(73) Assignee: The Board of Trustees of the Leland Stanford Junior University, Palo Alto, CA (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/133,948

(22) Filed: Aug. 14, 1998

(51) Int. Cl.[7] .................................................. G01B 5/28
(52) U.S. Cl. ................... 205/766; 423/445 R; 423/453; 73/105
(58) Field of Search ...................... 205/766; 423/445 R, 423/453; 73/105

(56) References Cited

U.S. PATENT DOCUMENTS

| | | | |
|---|---|---|---|
| 5,482,601 A | 1/1996 | Oshima et al. | 204/173 |
| 5,500,200 A | 3/1996 | Mandeville et al. | 423/447.3 |
| 5,780,101 A | 7/1998 | Nolan et al. | 427/216 |

FOREIGN PATENT DOCUMENTS

| | | | |
|---|---|---|---|
| EP | 913 508 A2 | * | 2/1998 |
| WO | 9510481 | | 4/1995 |
| WO | WO 98/05920 | * | 2/1998 |

OTHER PUBLICATIONS

Dai, H., "Nanotubes as nanoprobes in scanning probe microscopy," Nature, vol. 384, Nov. 14, 1996, pp. 147–149.

* cited by examiner

Primary Examiner—Kishor Mayekar

(57) ABSTRACT

The present invention includes several nanotube structures which can be made using catalyst islands disposed on a substrate (e.g. silicon, alumina, or quartz) or on the free end of an atomic force microscope cantilever. The catalyst islands are capable of catalyzing the growth of carbon nanotubes from carbon containing gases (e.g. methane). The present invention includes an island of catalyst material (such as $Fe_2O_3$) disposed on the substrate with a carbon nanotube extending from the island. Also included in the present invention is a pair of islands with a nanotube extending between the islands, electrically connecting them. Conductive metal lines connected to the islands (which may be a few microns on a side) allows for external circuitry to connect to the nanotube. Such a structure can be used in many different electronic and microelectromechanical devices. For example, a nanotube connected between two islands can function as a resonator if the substrate beneath the nanotube is etched away. Also, the present invention includes a catalyst particle disposed on the free end of an AFM cantilever and having a nanotube extending from the particle. The nanotube can be used as the scanning tip of the AFM as is know in the art.

45 Claims, 6 Drawing Sheets

CARBON NANOTUBE STRUCTURES MADE USING CATALYST ISLANDS

FIELD OF THE INVENTION

The present invention relates generally to the fabrication of nanotubes, and in particular to methods of fabricating nanotube structures from an array of catalyst islands on a semiconductor surface.

BACKGROUND OF THE INVENTION

Carbon nanotubes are recently discovered, hollow graphite tubules. When isolated, individual nanotubes are useful for making microscopic electrical, mechanical, or electromechanical devices. Obtaining individual, high quality, single-walled nanotubes has proven to be a difficult task, however. Existing methods for the production of nanotubes, including arc-discharge and laser ablation techniques, yield bulk materials with tangled nanotubes. The nanotubes in the bulk materials are mostly in bundled forms. These tangled nanotubes are extremely difficult to purify, isolate, manipulate, and use as discrete elements for making functional devices.

One conventional method for producing carbon nanotubes is disclosed in U.S. Pat. No. 5,482,601 issued to Oshima et al. on Jan. 9, 1996. The nanotubes are produced by successively repositioning a rod-like, carbon anode relative to a cathode surface such that a tip of the anode successively faces different portions of the cathode surface. A direct current voltage is impressed between the tip of the anode and the cathode surface so that an arc discharge occurs with the simultaneous formation of carbonaceous deposits containing carbon nanotubes on the cathode surface. The carbonaceous deposits are scraped and collected.

U.S. Pat. No. 5,500,200 issued to Mandeville et al. on Mar. 19, 1996 discloses a method for the bulk production of multi-walled tubes. According to the method, a catalyst is prepared using particles of fumed alumina with an average particle size of about 100 Å. Iron acetylacetonate is deposited on the alumina particles, and the resultant catalyst particles are heated in a hydrogen/ethylene atmosphere. The catalyst particles are preferably reacted with the hydrogen/ethylene mixture for about 0.5 hours in a reactor tube, after which the reactor tube is allowed to cool to room temperature under a flow of argon. Harvesting of the carbon tubes so produced showed a yield greater than 30 times the weight of the iron in the catalyst particles.

Although the methods described by Oshima and Mandeville are effective for producing bulk amounts of carbon tubes or carbon fibrils, the resulting bulk materials are "hairballs" containing tangled and kinked tubes which one collects into vials or containers. These bulk materials are useful to put into polymers or metals to make composites that exhibit improved properties of the polymers or metals. For making functional microscopic devices, however, these bulk materials are nearly useless because it is nearly impossible to isolate one individual tube from the tangled material, manipulate the tube, and construct a functional device using that one tube. Also, many of the tubes have molecular-level structural defects which results in weaker tubes with poor electrical characteristics.

Atomic force microscopes (AFMs) sometimes employ nanotubes as the scanning tip because nanotubes are resilient and have an atomically sharp tip. However, the manufacturing of nanotube-tipped AFM devices is problematic because the nanotubes must be painstakingly separated from disorganized bundles of nanotubes and attached to the AFM cantilever. It would be an advance in the art of atomic force microscopy to provide a nanotube-tipped AFM device that is simpler to manufacture.

OBJECTS AND ADVANTAGES OF THE INVENTION

In view of the above, it is an object of the present invention to provide a method for the large scale synthesis of individual distinct single-walled nanotubes. In particular, it is an object of the present invention to provide such a method which allows nanotube growth to be confined to desired locations so that the nanotubes can be easily addressed and integrated into structures to obtain functional microscopic devices. It is a further object of the invention to provide a method for integrating the nanotubes into semiconductor microstructures to obtain a variety of nanotube devices. Further, it is an object of the present invention to provide a nanotube-tipped atomic force microscope device which is simple to manufacture.

These and other objects and advantages will become more apparent after consideration of the ensuing description and the accompanying drawings.

SUMMARY

These objects and advantages are provided by an apparatus including a substrate and a catalyst island disposed on the substrate. The catalyst island includes a catalyst particle that is capable of growing carbon nanotubes when exposed to a hydrocarbon gas at elevated temperatures. A carbon nanotube extends from the catalyst particle. The nanotube may be in contact with a top surface of the substrate.

The substrate may be made of silicon, alumina, quartz, silicon oxide or silicon nitride. The nanotube may be a single-walled nanotube. The catalyst may include $Fe_2O_3$ or other catalyst materials including molybdenum, cobalt, nickel, or zinc and oxides thereof (iron molybdenum, and ruthenium oxides are preferred). The catalyst island is preferably about 1–5 microns in size.

The present invention also includes an apparatus having a substrate with two catalyst islands and a nanotube extending between the islands. The nanotube provides an electrical connection between the islands, which are electrically conductive. Conductive lines can provide electrical connections to the islands and nanotube. The nanotube may be freestanding above the substrate. A freestanding nanotube can be used as a high frequency, high-Q resonator.

Alternatively, one of the islands is replaced with a metal pad that does not have catalytic properties.

The present invention also includes an atomic force microscopy apparatus that has a catalyst particle disposed on a free end of a cantilever. A nanotube extends from the catalyst particle. The nanotube can be used as the scanning tip of the atomic force microscope apparatus.

The present invention also includes a method of making individually distinct nanotubes on a substrate surface. The method begins with disposing catalyst islands on the surface of a substrate. Then, the catalyst islands are contacted with methane gas at elevated temperature. The nanotubes grown are separate and extend over the surface of the substrate. The separate and distinct nanotubes can be incorporated into microelectronic or microelectromechanical devices.

DETAILED DESCRIPTION

Figure 1:
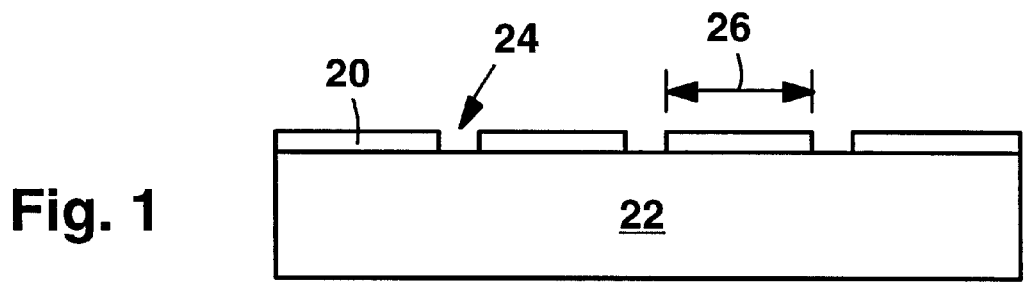
FIG. 1 shows a first step in making nanotubes according to the present invention.

FIG. 1 shows a first step in a method of the present invention for making individual carbon nanotubes which are individually separable and distinct. A layer of resist 20 is disposed and patterned on a top surface of a substrate 22. Patterning can be performed by e-beam lithography. The substrate 22 can be made of silicon, alumina, quartz, silicon oxide or silicon nitride for example. The substrate can also have a metal film on top.

The patterned resist 20 has holes 24 which expose the underlying substrate 22. The holes 24 are about 3–5 microns in size and spaced apart by a distance 26 of about 10 microns. The resist may have a single hole or many holes 24.

Figure 2:
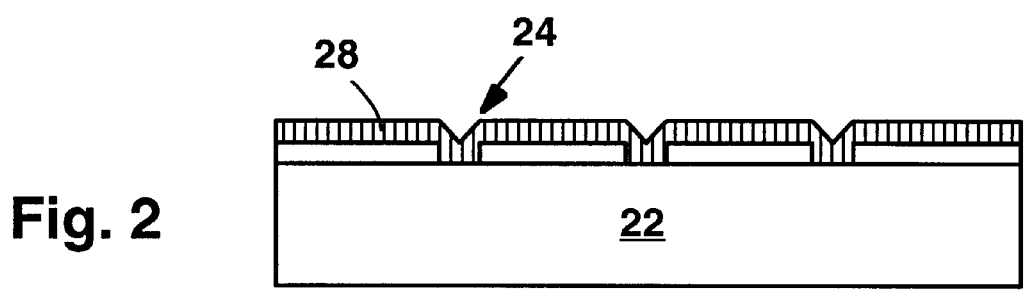
FIG. 2 shows a second step in making nanotubes according to the present invention.
Figure 3:
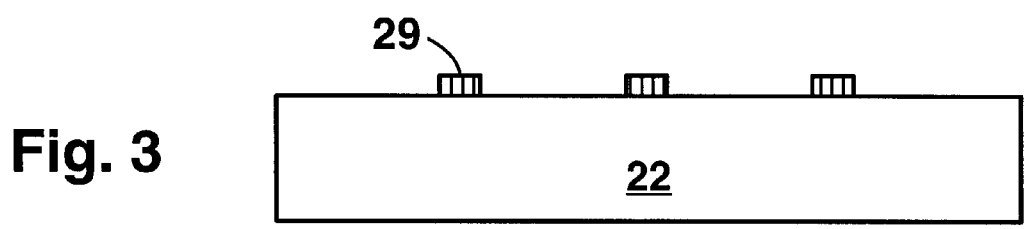
FIG. 3 shows a third step in making nanotubes according to the present invention.
Figure 4:
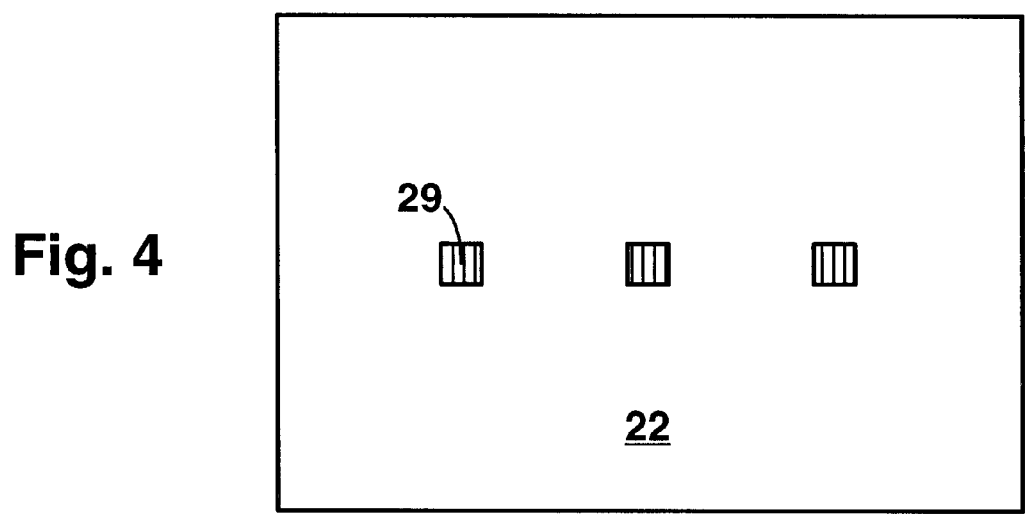
FIG. 4 shows a top view of a substrate with three catalyst islands.

Next, in FIG. 2, a solution of $Fe(NO_3)_3$ in methanol, mixed with alumina nanoparticles (about 15–30 nanometers in size, for example) is deposited on the surfaces of the resist 20 and substrate 22. In a specific example, catalyst preparation includes mixing 4.0 grams of alumina nanoparticles with 1.0 gram of $Fe(NO_3)_3*9H_2O$ in 30 mL methanol for 24 hours. After applying the mixture to the substrate, the solvent (i.e. methanol) is evaporated, leaving alumina nanoparticles coated with metal salt (i.e. $Fe(NO_3)_3$) 28 adhering to the resist and in the holes 24. Next, in FIG. 3, a lift-off process is performed, leaving isolated (nonconnected) islands 29 of $Fe(NO_3)_3$-coated nanoparticles adhering in regions where holes 24 existed. FIG. 4 shows a top view of the islands 29.

Heating the substrate 22 and nanoparticles decomposes the $Fe(NO_3)_3$ to $Fe_2O_3$. This is performed by placing the substrate in a furnace with an Argon atmosphere and heating to about 100–400° Celsius. The $Fe_2O_3$/nanoparticle mixture is an active catalyst which will catalyze the formation of carbon nanotubes when exposed to methane gas at elevated temperature.

Growth of single-walled nanotubes is performed by heating the substrate with catalyst islands in the furnace at about 850–1000° C. and flowing 99.99% pure methane over the catalyst islands 29 at a velocity of about 2–20 centimeters per second (e.g., for a 1-inch diameter tube, flowing methane at a rate of about 600–6000 $cm^3$/min). Use of these parameters results in nanotubes which are substantially perfect and straight, with no structural flaws (i.e. all the carbon rings in the nanotubes have 6 carbon atoms instead of 5 or 7 carbon atoms). Most of the nanotubes are single-walled, with diameters in the range of about 1–5 nanometers. When grown at 1000° C., 90% of the tubes were single-walled; when grown at 900° C., 99% of the tubes were single-walled. Most of the nanotubes have diameters in the range of 1–2 nanometers. The nanotubes have large aspect ratios (length/diameter) approaching about 10,000, and are very straight (a result of the absence of structural flaws).

It is noted that many different recipes for nanotube catalysts are known in the art. For example, $Fe(SO_4)$ or other Iron salts can be substituted for the $Fe(NO_3)_3$. The quality of the nanotubes depends upon the catalyst material used. Iron, molybdenum and zinc oxides are preferred for making high quality tubes. A particularly good catalyst is made with a mixture of iron, molybdenum and ruthenium oxides. Most generally, both elemental metals and their oxides can be used to grow nanotubes.

Also, the nanoparticles can be made of many ceramic materials besides alumina. Silica, for example, can also be used. Generally, refractory oxide ceramic materials can be used in place of the alumina nanoparticles. Still further, nanoparticles may not be used at all. Small quantities of Iron salts can be deposited on the substrate (for example, by dissolving in a solvent and evaporating the solvent) and heated to decomposition without being mixed with nanoparticles.

Figure 5:
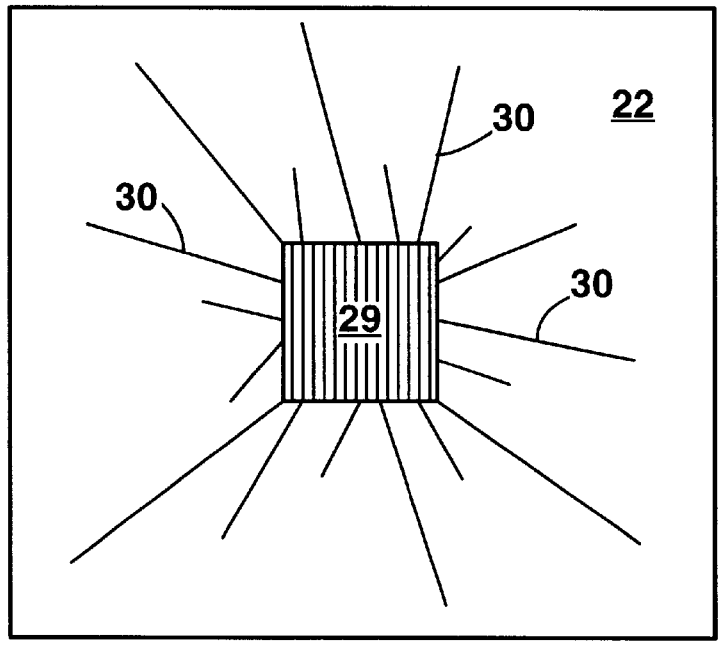
FIG. 5 shows a closeup top view of a single catalyst island which has been used to grow nanotubes.

FIG. 5 shows a closeup top view of the island 29 and substrate after the growth of nanotubes has been performed. Carbon nanotubes 30 extend from the island 29 in random directions. The carbon nanotubes 30 are not freestanding, but are disposed in contact with the substrate surface. Also, the carbon nanotubes are firmly attached to the island 29. The nanotubes generally grow in a 'base-growth' mode, where new carbon is added to the nanotubes 30 at the point where they are attached to the island 29. The nanotubes are attached at one end to the island, and the opposite end is free. The nanotubes can be used as resonators by allowing the free end to vibrate.

The carbon nanotubes 30 are not tangled together, but are individually separable. This is due to the fact that a small number of nanotubes grow from each island. Also, the nanotubes are spaced apart by a substantial distance. Typically, about 10–50 nanotubes are grown from each island. If larger numbers of nanotubes are grown (e.g. by using a more effective catalyst), then the nanotubes may form bundles. This is undesirable for applications requiring single distinct nanotubes. However, bundles of nanotubes can also be useful for many electrical and mechanical devices such as interconnects, field effect transistors, single electron transistors, and resonators which have only one fixed end.

Individually separable nanotubes are useful for the manufacturing of electronic and micromechanical devices because individual nanotubes can be incorporated into the devices by appropriately locating islands 29. Electrical and mechanical connections can be made to individual nanotubes if they are spatially separated and distinct.

Figure 6:
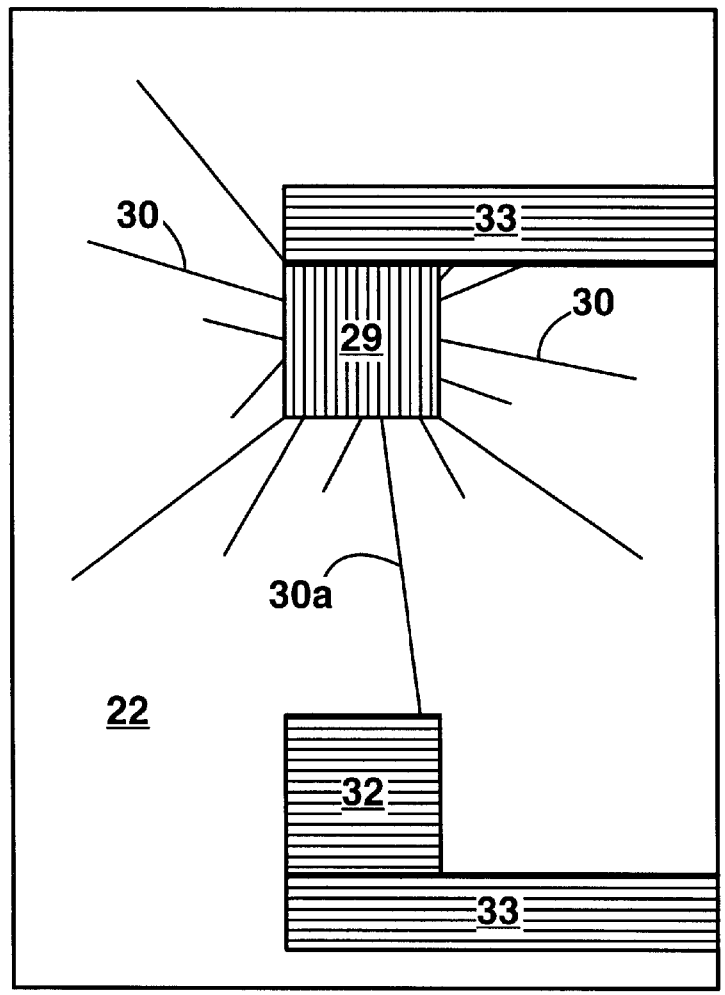
FIG. 6 shows an apparatus according to the present invention which has a nanotube connected between a catalyst island and a metal pad.

FIG. 6 shows a top view of an electronic device made by locating the island 29 close to a patterned metal pad 32. A single nanotube 30a extends from the island 29 to the metal pad 32, thereby providing electrical contact between the island 29 and pad 32. The island 29 and pad 32 are spaced apart by a distance in the range of 100 nanometers to about 5 microns. The island 29 and pad 32 are both electrically conductive, so patterned conductive lines 33 on the substrate surface can provide for macroscopic electrical connections to the nanotube 30a. The nanotube 30a with a macroscopic electrical connection on each end can be used in many devices including field-effect transistors, single electron transistors, or low current value fuses.

The conductive lines 33 may be applied to the substrate 20 before the islands 29 are deposited. In this way, the islands rest on top of the conductive lines 33. Also, the conductive lines 33 can be disposed on top of the islands (by applying the conductive lines on top of the islands. The conductive lines can be deposited before or after the growth of nanotubes.

The apparatus of FIG. 6 is made by simply locating the island and metal pad proximate to one another and catalytically growing nanotubes from the island. The closer the island 29 and pad 32, the more likely that a nanotube will be grown that connects the island and pad.

Also, two or more nanotubes can simultaneously electrically connect the island 29 and metal pad 32. If multiple nanotubes connect between the island and pad, then all but one of the nanotubes can be broken with an AFM tip. This is performed by dragging the AFM tip across the substrate surface so that it bends unwanted nanotubes until they break.

Further, a second catalyst island can be substituted for the metal pad 32. In such a device, the nanotube 30a provides electrical contact between two catalyst islands 29 instead of between an island 29 and a metal pad 32. Metal lines 33 can provide electrical connections to each catalyst island as in FIG. 6. The same spacing distance can be used (100 nanometers to about 5 microns) if a catalyst island is substituted for the metal pad.

Figure 7:
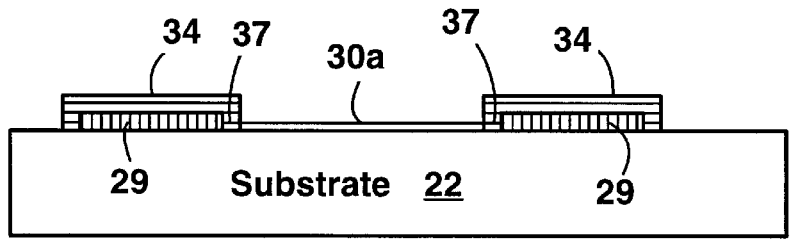
FIG. 7 shows a preferred embodiment of the present invention in which metal covers are disposed on top of the catalyst islands and portions of the nanotubes.

FIG. 7 shows a side view of a preferred embodiment of the present invention in which a metal cover 34 is deposited on top of each catalyst island 29. The metal covers 34 can be made of platinum or titanium-gold alloy, for example. Each metal cover 34 covers a portion of each island 29 and covers an end portion 37 of the nanotube 30a. The metal cover therefore serves to help hold the nanotube 30a rigidly in place.

The metal covers 34 help to provide Ohmic electrical connections to the ends of the nanotube 30a. Ohmic electrical connections with the nanotube are assured by heating the apparatus after depositing the metal covers 34. For example, heating the apparatus to about 300° C. in air will result in Ohmic electrical connections between the metal covers 34 and nanotube 30a. Metal lines 33 as shown in FIG. 6 can be connected to the metal covers to provide macroscopic electrical connections with the nanotube 30a. Electrical conduction through the catalyst island is therefore not necessary.

Figure 8A:
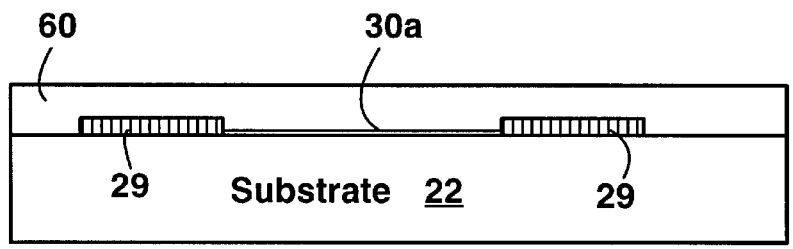
FIG. 8A–8C illustrate how the metal covers of FIG. 7 can be made.
Figure 8B:
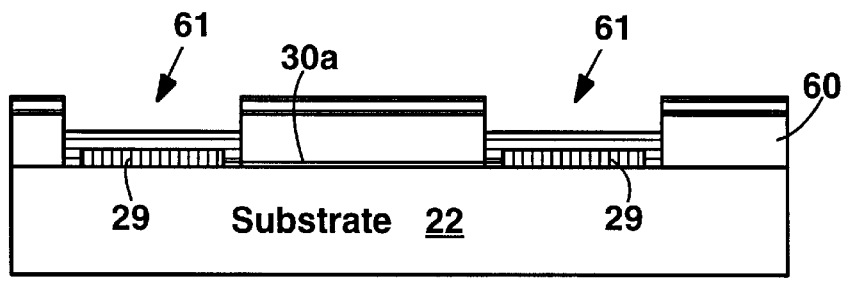
Figure 8C:
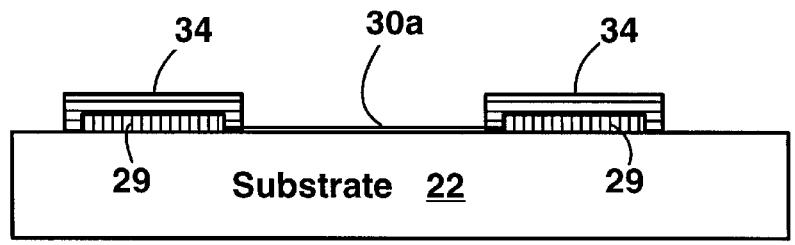

The metal covers 34 can be made by lithographically patterning the metal comprising the covers 34. FIGS. 8A–8C illustrate how this can be done. First, a layer of spin-on resist 60 is deposited on top of the islands 29 and nanotube 30a. Next, the resist 60 is etched in regions 61 where the metal cover 34 is to be located. The metal comprising the metal covers 34 is then deposited (by physical vapor deposition or CVD processes, for example), and the resist 60 is removed in a lift-off process which leaves only the metal covers 34.

Figure 9:
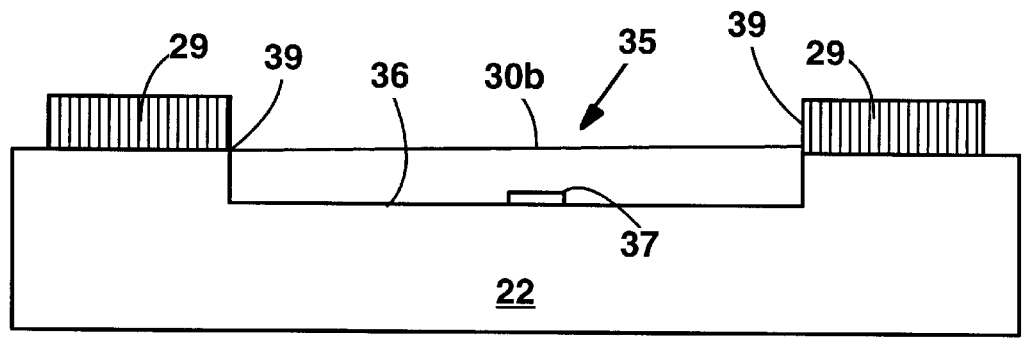
FIG. 9 shows a side view of a resonator according to the present invention made from a freestanding nanotube supported by the ends of the nanotube.

The present invention can provide freestanding nanotubes capable of acting as high-Q resonators. FIG. 9 shows a side view of a device including a freestanding nanotube 30b. The freestanding nanotube 30b is suspended above the substrate 22 which is depressed in a trench region 35 between the islands 29. The trench 35 can be formed by etching the substrate. The nanotube 30b therefore lies above a surface 36 of the etched substrate 22 and is supported only by nanotube ends 39. The trench 35 and metal covers 34 can be combined in the same apparatus.

The nanotube 30b can be resonated by locating the nanotube 30b in a magnetic field (perpendicular to the length of the nanotube 30b) and passing an oscillating current through the nanotube. A conductive film 37 capacitively coupled with the nanotube 30b extracts a resonant signal from the nanotube. Alternatively, the conductive film 37 can be used to electrostatically excite mechanical vibrations in the nanotube 30b.

Figure 10:
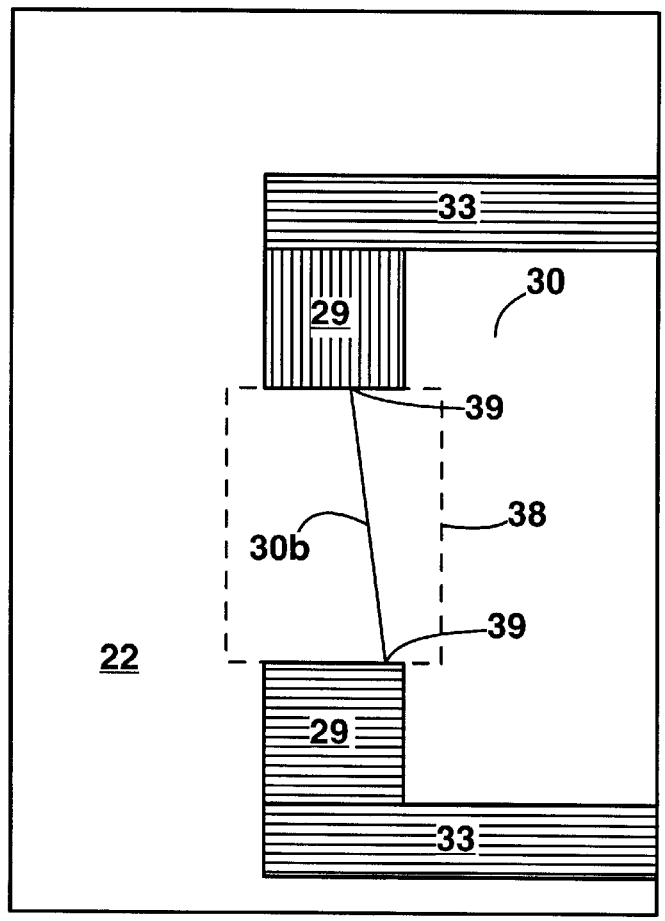
FIG. 10 shows a top view illustrating how the apparatus of FIG. 9 can be made.

FIG. 10 shows a top view of the substrate 22 and islands 29 illustrating how the apparatus of FIG. 9 can be made. First, the nanotube 30b which connects the islands 29 is grown. Other nanotubes will also be grown from both islands, but they are not shown for clarity. Then, all regions of the substrate except for a region defined by a box 38 are masked with resist. Spin-on resist can be used, for example. The act of spin-coating resist on the substrate will not damage the nanotube 30b. Next, the region inside the box 38 is exposed to an etchant which removes substrate material, but does not affect the nanotube 30b. Many different etchants can be used, depending upon the composition of the substrate (e.g. hydrofluoric acid can be used to etch $SiO_2$ or Si substrates). Etching the substrate 22 under the nanotube 30b results in the nanotube being supported only at its ends 39. Metal lines 33 provide macroscopic electrical connections to the nanotube 30b through the catalyst islands 29. Also, metal covers 34 can be deposited before or after etching the trench 35 to provide Ohmic electrical connections to the nanotube and improved mechanical stability for the nanotube ends 39.

Figure 11A:
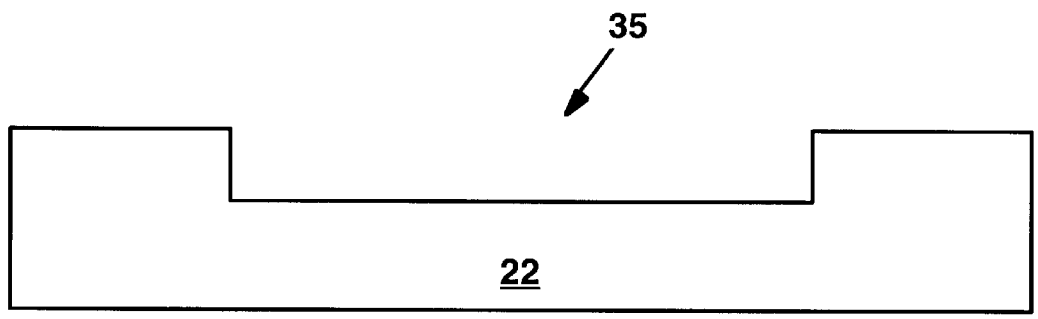
FIGS. 11A and 11B illustrate an alternative method of making the apparatus of FIG. 9.
Figure 11B:
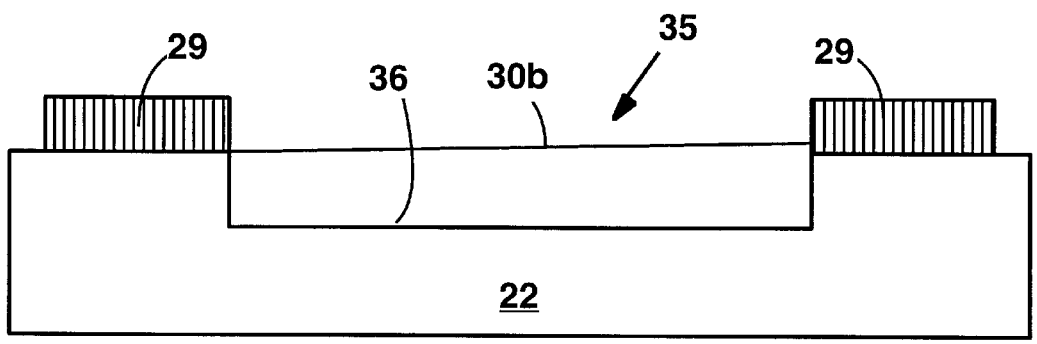

An alternative method for making the apparatus of FIG. 9 is shown in the side views of FIGS. 11A and 11B. In FIG. 11A, the substrate 22 is etched to form the trench 35 where the nanotube 30b is suspended. Then islands 29 are disposed on opposite sides of the trench 35 and nanotubes are grown from the islands 29. The nanotube 30b that connects the islands grows from one island to the other. Alternatively, one of the islands can be replaced with the metal pad 32, in which case the nanotube grows from the island 29 to the pad 32. Also, metal covers 34 can be deposited on top of the nanotube 30b and catalyst islands 29.

The present invention includes an embodiment where the freestanding nanotube is only supported on one end by a catalyst island 29 (i.e. the freestanding nanotube does not extend all the way across the trench 35). The nanotube is therefore a cantilever, and can be used as a resonator.

It is noted that growing nanotubes between islands, or between an island and a metal pad is an uncertain endeavor. One cannot be sure that a particular arrangement of catalyst islands will result in a nanotube connection between a particular pair of islands, or how many nanotubes will connect. However, if a pair of islands are spaced less than about 10 microns apart, and are at least 1 micron wide, a nanotube is likely to connect the pair of islands. At least one bridging nanotube connection can be practically assured if a number of islands are disposed with various spacings in an array.

Figure 12:
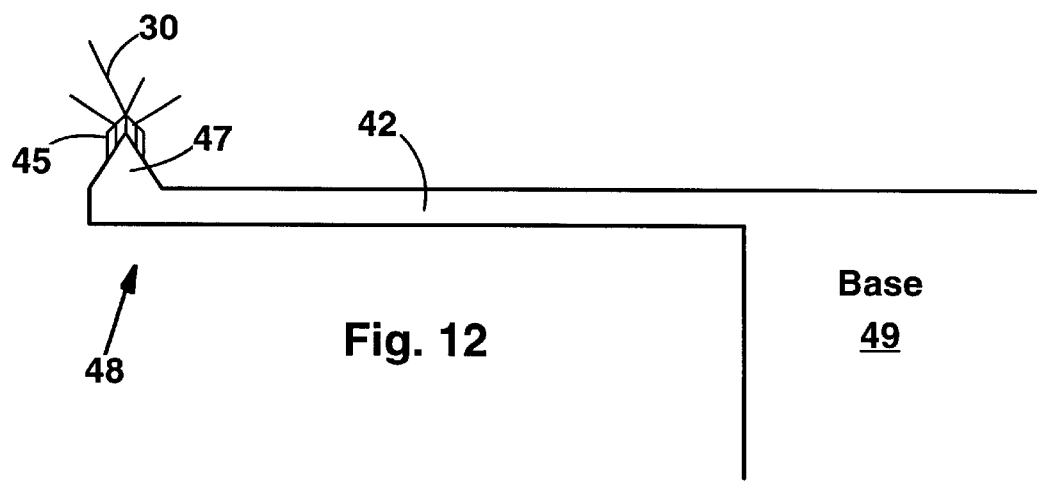
FIG. 12 shows an atomic force microscope tip made according to the present invention.

FIG. 12 shows another embodiment of the present invention in which a catalyst particle 45 is located on a tip 47 of an atomic force microscope (AFM) cantilever 42. The cantilever 42 is supported by a base 49, and has a free end 48 opposite the base 49. The particle 45 may be made of $Fe_2O_3$ (decomposed from $Fe(NO_3)_3$), for example. The catalyst particle 45 may or may not have supporting nanoparticles (i.e. silica or alumina particles). The catalyst particle is firmly attached to the tip 47. Nanotubes 30 grown from the particle 45 are firmly attached to the cantilever and are atomically sharp. Nanotubes grown from the catalyst particle can be used as probe tips for AFM. Alternatively, the cantilever does not have a tip 47, and the particle is disposed directly on the cantilever 42.

Figure 13A:
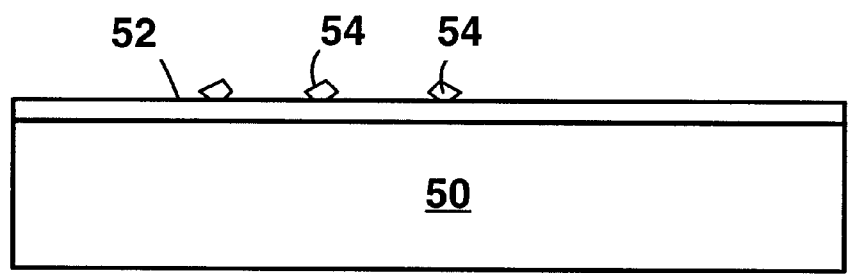
FIGS. 13A–13D illustrate a method of producing a carbon nanotube on a tip of an atomic force microscope cantilever according to the present invention.
Figure 13B:
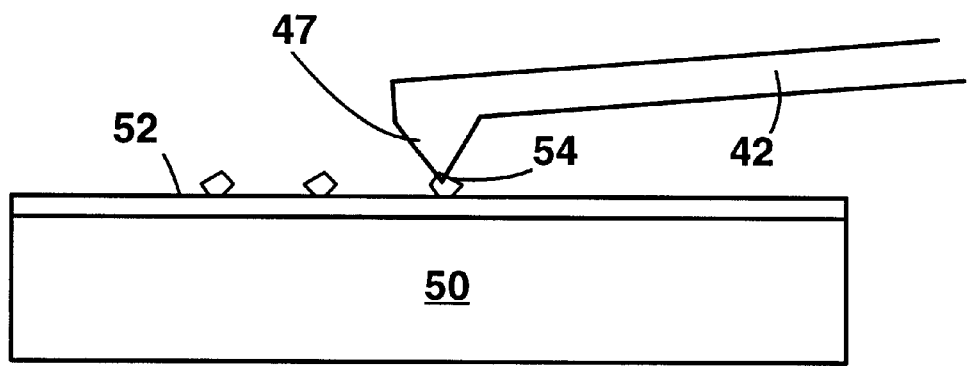
Figure 13C:
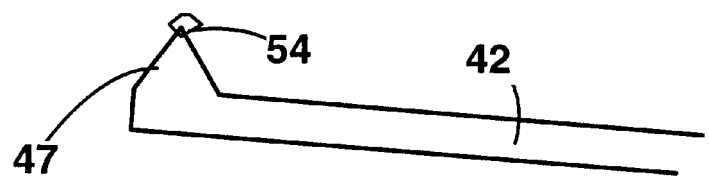
Figure 13D:
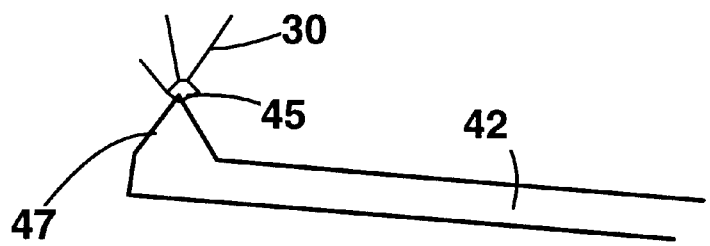

FIGS. 13A and 13B illustrate how the apparatus of FIG. 12 can be made. First, in FIG. 13A, a substrate 50 is coated with a gold film 52, and then droplets of $Fe(NO_3)_3$ dissolved in methanol are deposited on the gold surface. The methanol is then evaporated leaving only small particles 54 of $Fe(NO_3)_3$ on the gold film 52. Next, as shown in FIG. 13B, the AFM tip 47 is brought into contact with a particle 54 of $Fe(NO_3)_3$. An electric field is then applied between the tip 47 and the gold film 52. The electric field causes the $Fe(NO_3)_3$ particle to adhere to the tip 47 and may cause the $Fe(NO_3)_3$ to decompose into $Fe_2O_3$. Then, in FIG. 13C, the cantilever 42 and tip 47 with the adhered $Fe(NO_3)_3$ particle 54 is removed from the gold film 52. In FIG. 13D, the device is heated to fully decompose the $Fe(NO_3)_3$ particle 54 into $Fe_2O_3$. This transforms the $Fe(NO_3)_3$ particle 54 into a catalyst particle 45 (shown in FIG. 12). Then, nanotubes 30 are grown from the catalyst particle 45.

An AFM cantilever with a catalytically grown nanotube tip has several advantages over an AFM cantilever with a nanotube bonded with other techniques. It is a relatively simple task to catalytically grow a nanotube from the catalyst particle on the cantilever. Also, the nanotube is firmly bonded to the cantilever.

It will be clear to one skilled in the art that the above embodiment may be altered in many ways without departing from the scope of the invention. Accordingly, the scope of the invention should be determined by the following claims and their legal equivalents.

What is claimed is:

1. An apparatus comprising:
    a) a substrate with a top surface;
    b) a catalyst island disposed on the top surface of the substrate;
    c) a carbon nanotube extending from the catalyst island.
2. The apparatus of claim 1 wherein the nanotube is disposed on the top surface of the substrate.
3. The apparatus of claim 1 wherein the nanotube is a single-walled nanotube.
4. The apparatus of claim 1 wherein the catalyst island comprises $Fe_2O_3$.
5. The apparatus of claim 1 wherein the catalyst island comprises a material selected from the group consisting of iron, molybdenum, cobalt, nickel, ruthenium, zinc and oxides thereof.
6. The apparatus of claim 5 wherein the catalyst island comprises a material selected from the group consisting of iron, molybdenum, ruthenium and oxides thereof.
7. The apparatus of claim 1 wherein the catalyst island is in the range of 1–5 microns in size.
8. The apparatus of claim 1, wherein the substrate comprises a material selected from the group consisting of silicon, alumina, quartz, and silicon nitride.
9. The apparatus of claim 1 wherein the catalyst island comprises particles of ceramic material.
10. The apparatus of claim 1 further comprising a metal cover which covers an end portion of the nanotube and a portion of the island.
11. An apparatus comprising:
    a) a substrate with a top surface;
    b) two catalyst islands disposed on the top surface of the substrate;
    c) a carbon nanotube extending between the catalyst islands such that the nanotube provides an electrical connection between the catalyst islands.
12. The apparatus of claim 11 wherein the nanotube is disposed on the top surface of the substrate.
13. The apparatus of claim 11 wherein the nanotube is supported only by its ends.
14. The apparatus of claim 11 wherein the substrate comprises a trench under the nanotube so that the nanotube is freestanding.
15. The apparatus of claim 11 wherein the catalyst island comprises particles of ceramic material.
16. The apparatus of claim 11 further comprising a conductive line in electrical contact with each island.
17. The apparatus of claim 11 wherein the catalyst islands are separated by a distance less than about 50 microns.
18. The apparatus of claim 11, wherein the substrate comprises a material selected from the group consisting of silicon, alumina, quartz, silica and silicon nitride.
19. The apparatus of claim 11 wherein the catalyst islands comprise a material selected from the group consisting of iron, molybdenum, cobalt, nickel, ruthenium, zinc and oxides thereof.
20. The apparatus of claim 19 wherein the catalyst islands comprise a material selected from the group consisting of iron, molybdenum, ruthenium and oxides thereof.
21. The apparatus of claim 11 further comprising a metal cover which covers an end portion of the nanotube and a portion of at least one island.
22. An apparatus comprising:
    a) a substrate with a top surface;
    b) a catalyst island disposed on the top surface of the substrate;
    c) a metal pad disposed on the top surface of the substrate;
    d) a carbon nanotube extending between the catalyst island and the metal pad such that the nanotube provides an electrical connection between the catalyst island and metal pad.
23. The apparatus of claim 22 wherein the nanotube is disposed on the top surface of the substrate.
24. The apparatus of claim 22 wherein the nanotube is supported only by its ends.
25. The apparatus of claim 22 wherein the substrate comprises a trench under the nanotube so that the nanotube is freestanding.
26. The apparatus of claim 22 wherein the catalyst island comprises particles of ceramic material.
27. The apparatus of claim 22 further comprising a conductive line in electrical contact with the island.
28. The apparatus of claim 22 further comprising a conductive line in electrical contact with the metal pad.
29. The apparatus of claim 22, wherein the substrate comprises a material selected from the group consisting of silicon, alumina, quartz, silica and silicon nitride.
30. The apparatus of claim 22 wherein the catalyst island comprises a material selected from the group consisting of iron, molybdenum, cobalt, nickel, ruthenium, zinc and oxides thereof.
31. The apparatus of claim 30 wherein the catalyst island comprises a material selected from the group consisting of iron, molybdenum, ruthenium, and oxides thereof.

32. The apparatus of claim 22 further comprising a metal cover which covers an end portion of the nanotube and a portion of the island.

33. An apparatus comprising:
   a) a base;
   b) a cantilever extending from the base, the cantilever having a free end opposite the base;
   c) a catalyst particle disposed on the free end of the cantilever, wherein the catalyst particle is capable of catalyzing the growth of carbon nanotubes;
   d) a carbon nanotube extending from the catalyst particle.

34. The apparatus of claim 33 wherein the catalyst particle comprises $Fe_2O_3$.

35. The apparatus of claim 33 wherein the catalyst particle comprises a material selected from the group consisting of iron, molybdenum, cobalt, nickel, ruthenium, zinc and oxides thereof.

36. The apparatus of claim 33 further comprising a tip on the free end, wherein the catalyst particle is disposed on the tip.

37. The apparatus of claim 33 wherein the apparatus is an atomic force microscopy apparatus.

38. A method for producing an apparatus with a tip comprising a carbon nanotube, the method comprising the steps of:
   a) providing a cantilever suitable for use in atomic force microscopy;
   b) disposing a catalyst particle on a free end of the cantilever, wherein the catalyst particle is capable of growing carbon nanotubes when exposed to a carbon-containing gas at elevated temperature;
   c) contacting a carbon-containing gas to the catalyst particle at elevated temperature.

39. The method of claim 38 wherein step (b) comprises the steps of:
   i) contacting the free end to a particle of $Fe(NO_3)_3$ disposed on an electrically conductive substrate; and
   ii) applying an electric field between the free end and the substrate.

40. The method of claim 38 wherein step (b) comprises the steps of:
   i) contacting the free end to a particle of $Fe(SO_4)_2$ disposed on an electrically conductive substrate; and
   ii) applying an electric field between the free end and the substrate.

41. The method of claim 38 wherein the apparatus produced is an atomic force microscopy apparatus.

42. A method for producing individually distinct carbon nanotubes, the method comprising the steps of:
   a) providing a substrate with a top surface;
   b) forming an island of catalyst material on the top surface;
   c) heating the substrate and catalyst island; and
   d) contacting the catalyst island with a carbon-containing gas for a period of time sufficient to form the nanotubes on the catalyst island.

43. The method of claim 42 wherein the catalyst island is about 1–5 microns in size.

44. The method of claim 42, wherein the carbon-containing gas comprises methane.

45. The method of claim 42, wherein the period of time is about 10 minutes.

* * * * *